(12) United States Patent
Woo

(10) Patent No.: US 7,097,610 B2
(45) Date of Patent: *Aug. 29, 2006

(54) TREATMENT OF AFFLICTIONS, AILMENTS AND DISEASES

(76) Inventor: Gilson Woo, 19708 Balan Rd., Rowland Heights, CA (US) 91748

( * ) Notice: Subject to any disclaimer, the term of this patent is extended or adjusted under 35 U.S.C. 154(b) by 0 days.

This patent is subject to a terminal disclaimer.

(21) Appl. No.: 09/909,505

(22) Filed: Jul. 20, 2001

(65) Prior Publication Data

US 2001/0041820 A1   Nov. 15, 2001

Related U.S. Application Data

(63) Continuation-in-part of application No. 08/939,429, filed on Sep. 26, 1997, now abandoned.

(51) Int. Cl.
*A61N 1/00* (2006.01)

(52) U.S. Cl. ........................................................ 600/15

(58) Field of Classification Search ............. 600/9–15, 600/407; 128/898; 324/263; 2/113, 159, 2/160

See application file for complete search history.

(56) References Cited

U.S. PATENT DOCUMENTS

| | | | | | |
|---|---|---|---|---|---|
| 3,658,051 | A | * | 4/1972 | MacLean | 324/263 |
| 4,134,395 | A | * | 1/1979 | Davis | 600/407 |
| 5,529,569 | A | * | 6/1996 | Woo | 600/9 |
| 5,720,046 | A | * | 2/1998 | Lopez et al. | 2/159 |
| 5,782,743 | A | * | 7/1998 | Russell | 600/15 |
| 5,950,239 | A | * | 9/1999 | Lopez | 600/15 |
| 6,379,295 | B1 | * | 4/2002 | Woo | 600/15 |

* cited by examiner

*Primary Examiner*—Samuel G. Gilbert

(57) ABSTRACT

A method and apparatus for alleviating or curing human afflictions, ailments and diseases holistically by application of magnetism in such way of bringing the meridian systems into a balance and harmony. A north pole surface of a magnet is applied to a portion of the trunk, about 1204 square inches, of a person being treated, and is maintained in contact for a time period or periods in accordance with total flux applied for the afflictions or ailments being treated. The magnet is maintained in contact for a time period or periods sufficient to elicit holistic effect of alleviation or cure and to detect ailments and cure in progress or a balanced treatment point. Magnet is being configured to accommodate the area being treated and haying appropriate total flux of healing power.

18 Claims, 2 Drawing Sheets

TREATMENT OF AFFLICTIONS, AILMENTS AND DISEASES

This invention is a result of a series of findings in my research for magnetic treatment since 1980 from which a method for holistic therapeutic effect of entire body by application of magnetism only to the hands or the head or the neck of patient was either already patented or is in pending by USA Patent Office under the title of Treatment of Ailments, Afflictions and Diseases and the respective Patent number is U.S. Pat. No. 5,529,569 Jun. 25, 1996 and patent application Ser. Nos. 09/570/510 Jul. 13, 2000 and 09/722, 239 Apr. 28, 2001 which are the continuation-in-part of application Ser. No. 08/939,429 Sep. 26, 1997 now abandon.

BACKGROUND OF THE INVENTION

The present invention is directed to a method of applying magnetism only to the trunk of patient for holistic effect of entire body, which is not possible under the conventional method of prior art and Acupuncture Practice of Oriental Medicine.

The conventional method is holistically effective and applicable to all ailments of human body for concurrent treatment utilizing meridians of the hands, head and neck of Oriental medical theory and the brain control functions of self-survival healing mechanism. However, the trunk application is uniquely effective with local pains of abdomen, chest, back, loin/waist, lower extremity and related organs and parts along the respective meridian lines that run through the trunk which include bladder, gall bladder, stomach, pancreas/spleen, liver, kidney, conception, governing vessel and extra meridians of penetrating vessel, girdle vessel, yang heal vessel, eum heal vessel, yang linking vessel and eum linking vessel. The conventional method utilizes only hands, head and neck of person and the present invention utilizes only trunk of person or combined with head and neck in magnetic application. When the trunk application is utilized together with head and neck magnetic application, effectiveness is increased with far less treatment time and faster healing, especially helpful in relief of pains associated with muscle tension, stiffness, infalmmation and ill-symptoms of the organs in the region of body trunk and lower extremities.

This is a method of pain relief and cure for holistic effect of entire body by applying negative magnetic flux, North pole, only to the trunk portion of the body of the person treated, applying the principles of the Oriental Medicine utilizing the body's meridians known as pathway of life energy of the human body.

There are 12 main meridians and 8 extra vessel meridians, a total of 20, disposed throughout the entire human body and 730 acupoints assigned and scattered all over the body. Eighteen (18) meridians are bilateral and 2 meridians are unilateral, i.e., bilateral meridians are disposed symmetrically on both side of the body, left and right, their functions are exactly the same as a twin pair. Two (2) meridians are unilateral that run through the center of the front and backside of the body with a different function of governing negative and positive meridians respectively. The main meridians of the human body maintain a balance and harmony for all the organs of the body system in accordance with the five (5) element-functions of meridians of the dual power system of positive and negative energy force, which are based on Five (5) Elements of Law of Nature, consisting of "Wood", "Fire", "Earth", "Metal", and "Water" by which transform into meridians in a form of "help or helped by", "restrain or restrained by", and "harm or harmed by", which lead into two type of functioning—conflicting meridian and co-living meridian, and most afflictions of chronic type ailments are all associated with conflicting meridians. The conflicting meridians are harmful and not helpful to each other thus it is very difficult to maintain or bring the balance back to normal between conflicting meridians. Five Elements & Conflicting Meridians are as follows:

Five Elements:
Co-living Order. "help or helped by"—Wood, Fire, Earth, Metal, Water
Conflicted Order. "harm or harmed by"—Wood, Earth, Water, Fire, Metal
Conflicting Main Meridians:
Lung Meridian harms Liver Meridian
Large Intestine Meridian harms Gall Bladder Meridian
Kidney Meridian harms Heart Meridian
Bladder Meridian harms Small Intestine Meridian
Liver Meridian harms Spleen/Pancreas Meridian
Gall Bladder Meridian harms Stomach Meridian
Heart Meridian harms Lung Meridian
Small Intestine Meridian harms Large Intestine Meridian
Pericardium Meridian harms Lung Meridian
Three Triple Warmer Meridian harms Large Intestine Meridian
Spleen/Pancreas Meridian harms Kidney Meridian
Stomach Meridian harms Bladder Meridian These five elements are assigned to only 12 main meridians and five acupoints per main meridian for its function in terms of maintaining balance and order for each main meridian and its organs of the body. The non-element meridians and non-element acupoints are not capable of adjusting the balance of the meridian and are normally used only for local pain and lesion. Main meridians are all rooted on toes and fingertips, except the sole of foot for kidney meridian, with the energy flow orientation of either ascending from or descending to the toes and sole of the foot and fingertips of the hand, and its five-element acupoints are all located in the region of hand and lower arm and foot and lower leg.

Under Oriental Medicine, any affliction in chronic nature is believed to be a result of energy imbalance and disorder in terms of the dual meridian system of the body, therefore, "such afflictions of chronic ailments are treated only by adjusting meridians into a balance and harmony, otherwise, such ailment and pain from the energy imbalance and disorder are not healed or eradicated after all", quoted from the Text of the Oriental Medicine known as a "Golden Rule".

When the systems of the body are not in balance in view of the meridians and the dual power concept the body is in ill status in the related organs of the unbalanced meridians. When the systems of the body are well balanced, the body is in good health. Therefore, the therapy is directed toward stimulating or depressing the energy in the meridians concerned.

The method of present invention involves 2 unilateral and 6 bilateral meridians, and 6 extra meridians, and 36 unilateral acupoints and 95 bilateral acupoints that are being disposed through the entire body trunk, which are Governing Vessel of 14 acupoints, Conception Vessel of 22 acupoints, Bladder of 39 acupoints, Gall Bladder of 7 acupoints, Stomach of 19 acupoints, Kidney of 17 acupoints, Liver of 3 acupoints, Pancreas/Spleen of 10 acupoints whereas only hand, head and neck meridians are being utilized in the referenced prior art.

This method is also extremely effective in relieving pain, inflammation and distress associated with chronic ailments related with the complicated energy systems of the meridians of the trunk of the body. When magnetic fluxes are applied to the trunk as shown in the diagram of FIGS. 3, 4, 5, 6, 7, 8, 9, 10 and 11 of drawings for therapeutical effect, life energy pathways of the trunk meridians are directly affected.

These important elements of the energy flow channels are being stimulated or restored instantly, upon application of magnetism to the trunk, to elicit holistic therapeutical effect of entire body, thus breathing, circulation and energy flow are improved and order and balance of the energy system is restored to help body heals fast and relieves pains effectively, which are all observable and verifiable at sight.

This method enables body to sense responses from ill parts/locations and cure in progress in same way as the head, neck and two-hand method of the referenced prior art, whereas note there is no response being occurred or detected from the healthy body with no ailments by application of magnetism.

These phenomenal healing are identical to that of the Oriental Medicine so called "Myung-Hyun" defining as a positive body signal that the ailing part is definitely healing, which indicates the proper use of five element rules for meridains and balance concept of the dual power systems.

In addition, this phenomenon is believed to be some form of reaction of brain sick memory recall in response to the magnetic application and futher to indicate that,when body is in sickness, pathway of life-energy meridan and sensory neurons of the nervous system are being hindered by some form of blockage and, when the flow is stimulated by magnetic flux, the flow hindered causes responses and symptoms and, when the body is in health, the pathways are all clear and wide open for free flow thus causing no response or symptom even under magnetically stimulated condition in energy flow and neural transmission.

An evidence to support this fact is that, when pain and ailment are cured by magnetic flux, all such responses and symptoms are gone and disappeared.

Magnets and magnetism have heretofore been utilized in the treating of human disease and afflictions.

Any magnet configurated and sized to cover substantially the treatment area of the trunk can be used for this method as long as it produces a sedative and healing effect in a range of 30ϕ to 250,000ϕ total flux and the north pote surface is flat and smooth for good contact to the trunk. Total flux of up to 5,000ϕ is believed to be ideal for pain control and management of sedative effect and total flux of above 5,000ϕ is believed to be good for healing cure effect.

In comparison with the referenced method of prior art, this method of utilizing trunk is more beneficial in some ways: more effective in relieving pains of related meridians such as organs of liver and gall bladder, kidney and bladder and digestive systems covering abdomen, chest/ribs, back, waist/loin/hip, thigh, leg, foot, and easy off balanced treatment, etc.

Magnetic application in terms of alternative medicine or natural energy medicine has been widely recognized in the Western in recent years although this has been primarily an Oriental practice. Many innovative methods of magnetic treatment have been introduced, yet there is much left to be done for improvement.

Therefore, a general object of the present invention is to provide treatment for a wide variety of ailments and diseases for holistic effects, except for those requiring surgical treatment.

An object of the present invention is to provide such a method which utilizes magnetism applied to a portion of the trunk of a person, thus to provide concurrent treatment of a plurality of ailments and afflictions of the entire body for holistic effect.

An object of the invention is to provide such treatment utilizing magnetism in simplified methods that can be practiced without specialized professional knowledge.

An object of the invention is to provide such methods that provide recovery from fatigue and which provide energetic, vigorous feelings.

An object of the invention is to provide such methods that provide substantial cures, relief of pain and rapid healing.

An object of the invention is to provide such methods that provide breathing control and/or improved circulation of the blood of the person to allow an optimum condition of the body systems, An object of the invention is to provide methods and techniques of treatment utilizing magnetism, independently of meridians or acupuncture points according to Oriental medicine.

An object of the invention is the provision of such a method which is economical and effective.

An object of the invention is the provision of such methods which, properly utilized, are safe and involve no harm to a patient and no adverse reaction or sequelae.

An object of the invention is the provision of such methods which involve the effecting of a balance of the energy systems of the body, in accordance with Oriental medicine theories, in treating ailments and applications.

SUMMARY OF TH INVENTION

The foregoing object and advantages, as well as others which will be apparent from the specification, are achieved by a method for treating and alleviating human afflictions, ailments and diseases by the application of magnetism to a person being treated in such way to bring the meridians into a balance and harmony.

A north pole surface of a magnet is applied to the person, only to a portion of the trunk.

Contact with magnet is maintained for a sufficient time period or periods to provide substantial alleviation or cure.

The magnetic strength or total flux applied to the trunk may typically be from about 30ϕ to about 250,000ϕ total flux. The magnet may be maintained in contact with the person for a time period sufficient for the eliciting of substantial alleviation or cure. Magnet means are provided for application to the portion of the trunk of a person being treated, with a north pole surface of the magnet means configurated to engage the portion or the area of the trunk of the person.

DESCRIPTION OF THE PREFERRED EMBODIMENT

According to the present invention magnet or magnets are applied to the body trunk of the person being treated. The method of trunk magnetic treatment involves application of magnetism by attaching a magnet directly to the designated treatment area of the body trunk only to elicit holistic therapeutical effect of the body.

In utilizing the method, where affliction or chronic ailment is treated, the trunk is subjected to the magnetic treatment according to the invention.

The method is an effective and powerful method of holistic treatment. The affliction, ailments and diseases of the entire body of a person may be treated concurrently by application of magnet means to the area of the trunk of the person.

In this method, magnets are applied directly to the designated area of the trunk of a patient.

Figure 1:
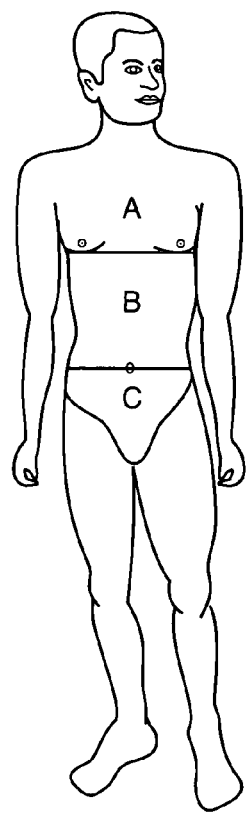
FIG. 1 is a perspective view showing a designated treating region utilized in the invention in the application of magnet means to the body trunk of a person.
Figure 2:
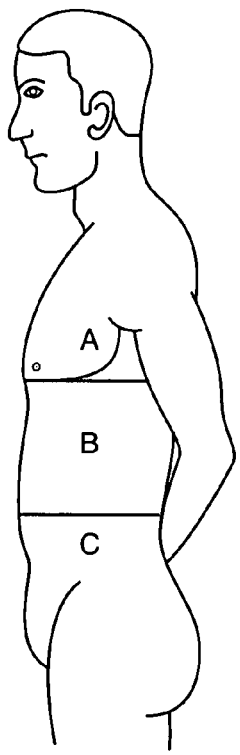
FIG. 2 is a perspective view showing a side trunk with a designated treating region utilized in the invention in the application of magnet means to the body trunk of a person.

A particular area of the trunk where the meiidians are disposed is being designated for holistic therapeutical effect and its size is about (559) 1204 square inches, (43) 28 inches long and (13) 43 inches wide reflecting an entire area of the trunk of the body of a person, as shown in FIGS. 1 and 2.

The designated area of the trunk covers all the way around its trunk in about (13") 43" wide, and many meridians are being disposed in the area of the body trunk. The governing vessel meridian is disposed through the median line of the spinal column which is the intermediate line of the back part of the body, and the Conception meridian is disposed through the navel of the body which is the intermediate line of the front part of the body, and the meridians of Bladder, Gall bladder, Stomach, Pancreas/Spleen, Liver, Kidney, and Extra meridians of Penetrating Vessel, Girdle Vessel, Yang Heal Vessel, Eum Heal Vessel, Yang Linking Vessel and Eum Linking Vessel are disposed on both side of the front and back median lines of the trunk. Thus, there are 2 unilateral meridians and 12 bilateral meridians, altogether 14 meridians, and 36 unilateral acupoints and 95 bilateral acupoints, altogether 131 acupoints, that are being disposed in the designated area involving the trunk method of holistic treatment. However, the 131 acupoints on the trunk area are normally used by acupuncture technics to treat the ailments associated with local pains of trunk and its meridian and organ, and they provides no means of holistic effects of entire body. But by applying magnetism to the area as a whole in accordance with the invention provides an effective means of holistic therapeutical effect of whole body.

In order to elicit such a holistic therapeutical effective and balanced treatment, the whole area of the round trunk may be divided into 3 regions such as chest and upper back region "A", upper abdominal and middle back region "B" and lower abdominal and lower back region "C" of the trunk by drawing a horizontal line across around the entire trunk of the body from the plexus and navel of the body, as shown in FIG. 1 and 2 of the drawings.

The designation of three sub-regions in the trunk for balance treatment of meridians and its organs is based on the five (5) element rules of meridians and acupoints and the balance concept of the dual power systems of positive and negative meridians of acupuncture practice, which are the essential factors in controlling the enemy flow state of meridians of the body, and the physical location of the organs related with the five (5) element rules of meridians in conflict are also considered for defining the treating regions.

A total of 12 organs are positioned in the trunk area in a conflict manner between organs of conflict meridians, the body trunk is thus divided into three treating regions of chest, upper abdomen and lower abdomen for balance treatment as shown below.

1. Chest Region—chest area of the upper trunk (arm, shoulder, neck regions are excluded):
   Heart, Lung, Pericardium—conflicted meridians
2. Middle Region—upper abdomen area:
   Gall Bladder, Liver, Stomach, Spleen/Pancreas, Kidney—conflicted meridians
3. Lower Region—lower abdomen area:
   Bladder, Small Intestine, Large Intestine, Three Triple Warmer—conflicted meridians In order for proper control of the conflicted meridians and its organs in terms of an equilibrium and balance, the trunk is divided into 3 sub-regions thus enabling a balanced treatment for either by each region or all regions concurrently in safe without causing any situation of imbalance in the treatment regions as well as the respective meridians. Each region has a distinctive characteristic in treatment and effectiveness:

The Chest Region is for treating the conflicted meridians and its organs of the Lung, Heart and Pericardium in safe concurrently—under the ordinary acupuncture technique it is almost impossible to treat these conflicted organs and meridians concurrently without side effect:

The Middle Region is for treating the conflicted meridians and its organs of the Gall Bladder, Liver, Stomach, Spleen/Pancreas and Kidney in safe and concurrently—under ordinary acupuncture technique it is almost impossible to treat these conflicted organs and meridians concurrently without side effect:

The Lower Region is for treating the conflicted meridians and its organs of the Bladder , Small Intestine, Larae Intestine and Three Triple Warmer in safe and concurrently—under ordinary acupuncture technique it is almost impossible to treat these conflicted organs and meridians concurrently without side effect.

These regions of the trunk are treated horizontally along the way around the trunk by applying magnet or magnets in horizontal order in parallel to the sub-regional division lines.

Figure 3:
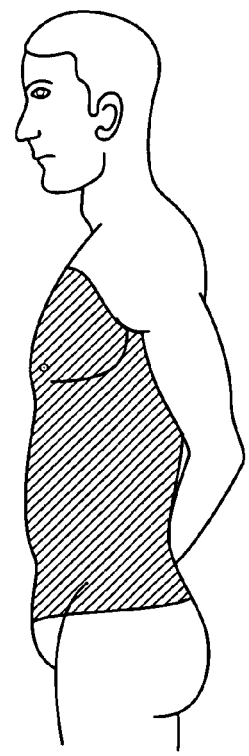
FIG. 3 is a perspective view showing the application of trunk of a person to magnet means of applying a magnet to the entire area of the body trunk.
Figure 4:
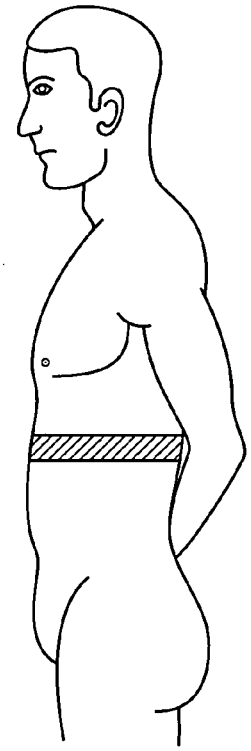
FIG. 4 is a perspective view showing the partial application of magnet means with a magnet to a subregion of the trunk of a person in horizontal order.
Figure 5:
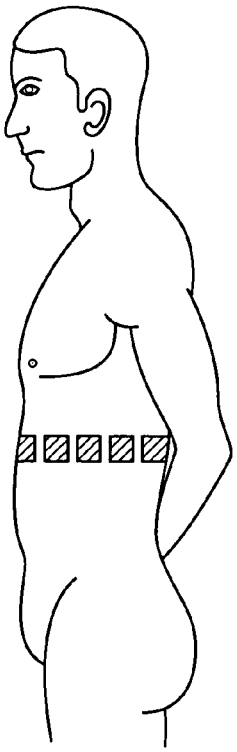
FIG. 5 is a perspective view showing the partial application of magnet means with multiple magnets to a subregion of the trunk of a person concurrently in horizontal order.

Thus, all meridians disposed in the body trunk are affected simultaneously and equally in balance, regardless of what subregion or horizontal zone is used, and thereby afflictions of all ailments related with the trunk meridians and its organs are treated concurrently and holistically. All regions of the trunk may be treated together as a whole, as shown in FIG. 3, or partially by region at a time independently or consecutively, as shown in FIGS. 4 and 5, or partially by all regions together, as shown in FIGS. 6, 7, 8, 10 and 11 of the drawings.

The region "A" is preferably utilized when chest or upper back is in pain or sick, and the region "B" is preferably utilized when upper abdomen or middle back is in pain or sick, and the region "C" is preferably utilized when lower abdomen or lower back is in pain or sick.

When chest all back and all abdomen are in pain or sick, use all subregions concurrently, or just use "A" or "B" or "C" region alone independently because it all produces a holistic effectiveness for the entire body. This trunk method may be utilized with the head and neck method together concurrently to increase effectiveness with less time of treatment which is extremely helpful especially in relieving pains in the region of chest, abdomen, back, spinal column and lower extremities, and symptoms of inflammation, stomach trouble, diarrhea, lumbago, cramp, neuralgia, etc.

Figure 6:
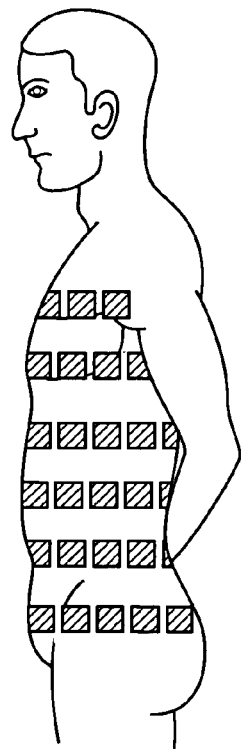
FIG. 6 is a perspective view showing the partial application of magnet means with multiple magnets to all subregions of the trunk of a person together concurrently in horizontal order.
Figure 7:
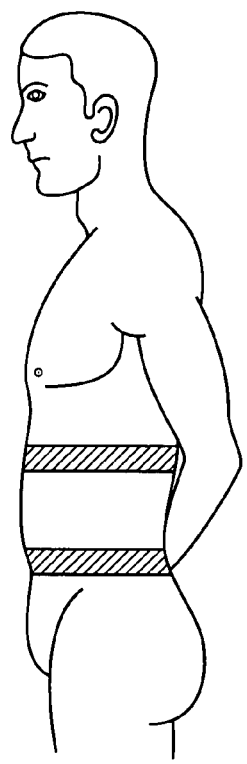
FIG. 7 is a perspective view showing the partial application of magnet means with a magnet to two subregions of the trunk of a person concurrently in horizontal order.
Figure 8:
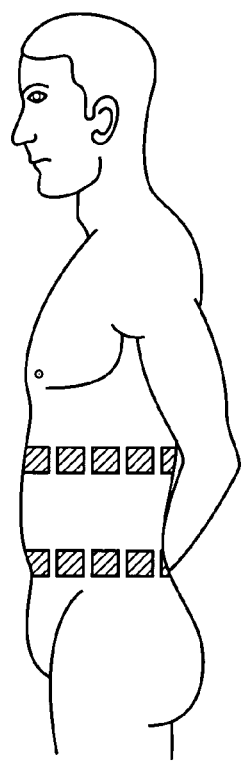
FIG. 8 is a perspective view showing the partial application of magnet means with multiple magnets to two subregions of the trunk of a person concurrently in horizontal order.
Figure 10:
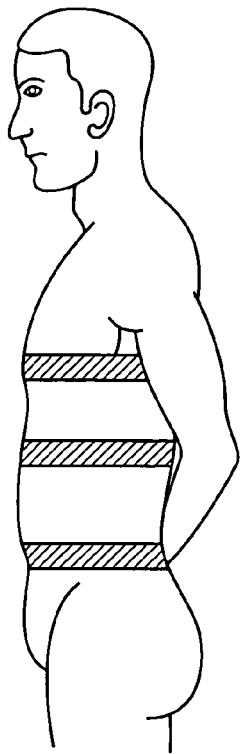
FIG. 10 is a perspective view showing the partial application of a magnet means with a magnet to all subregions of the trunk of a person concurrently in horizontal order.
Figure 11:
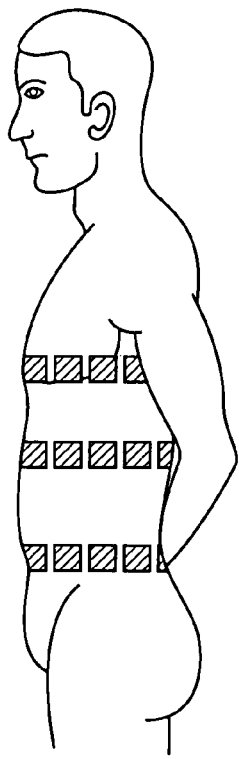
FIG. 11 is a perspective view showing the partial application of a magnet means with multiple magnets to all subregions of the trunk of a person concurrently in horizontal order.
Figure 12:
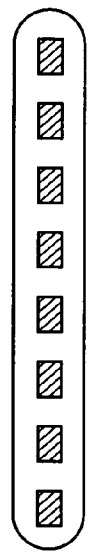
FIG. 12 is a perspective view showing a trunk band utilized for a partial concurrent treatment with multiple magnets for a region of the trunk of a person.

The method of trunk treatment by utilizing magnet or magnets are described as follows; Magnet or magnets are attached directly to the trunk in the designated area, as shown in FIGS. 3, 4, 5, 6, 7, 8, 10 and 11 of the drawings. The magnet or magnets may be applied evenly to the entire treating area all the way around the trunk in parallel to the horizontal subregional lines, concurrently with an equal total flux, as shown in FIGS. 2 and 6 of the drawings, or partially by region at a time, as shown in FIGS. 4 and 5 of the drawings, independently or consecutively one by one with an equal total flux and an equal amount of treatment time, or partially by all regions together concurrently, as shown in FIGS. 10 and 11 of the drawing, with an equal total flux and an equal amount of treatment time.

In utilizing partial treatment by region at a time, or all regions together, balanced treatment should be practiced by using an equal total flux and an equal amount of treatment time.

Partial treatment may be practiced with any number of magnets sized more than ⅛" in diameter. Number of magnets used is determined by size and total flux of the magnet based on repelling and pulling power.

Figure 9:
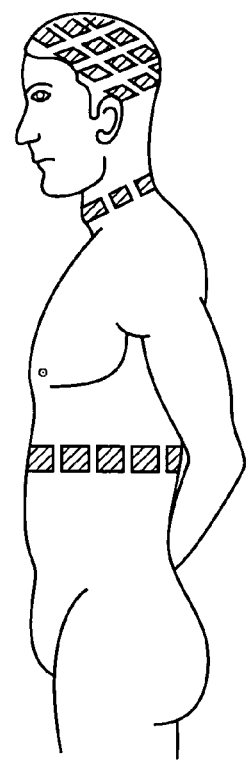
FIG. 9 is a perspective view showing a combined treatment of trunk, neck and head together concurrently.

Small size is lighter and convenient in use enabling more coverage of treating area and thereby smaller size with higher total flux is always preferable in treatment. When applying multiple magnets for partial treatment of a region or regions together, magnets are placed and spaced apart one another at an equal distance through out a region or regions of the trunk, in parallel with the horizontal subregional line, as shown in FIGS. 4, 5, 6, 7, 8, 10 and 11 of the drawings, so that magnets are placed evenly around the trunk of the body. Thus, all parts of the trunk and its meridians are treated equally of total flux for balanced treatment. When utilizing a combined method of the trunk, neck and head together, magnets should be applied concurrently in same way as to produce a balanced treatment effect for all regions involved with the combined method, as shown in FIG. 9, with same total flux and an equal amount of treatment time. In the case of using the combined method, applying magnets by region consecutively at a time is not appropriate because too many meridians are involved with the trunk, neck and head that make difficult to achieve a balanced treatment.

In applying magnetism to the trunk of a patient, the magnets are preferably configured and sized to cover partially or substantially the regional area of the body trunk, and preferably to cover substantially around the entire regions of the trunk of the patient. Only the north pole of a magnet is applied.

In utilizing the area in the regions in application to the body trunk of a patient, it is typically and ordinarily necessary, in order to avoid a imbalance treatment in accordance with the Oriental medical theory, to apply magnet or magnets with an equal total flux for each and all treating area of the regions with an equal amount of treatment time for a balanced treatment for respective meridians.

And, in addition, the balanced concept should also be applied by using the median line of the body which divides the trunk into a half, left and right, and the horizontal lines dividing the trunk into three parts, in order to avoid an imbalance condition of the body meridian systems.

Accordingly, when applying magnet or magnets around the trunk in parallel to the horizontal lines, always place the magnets evenly at an equal distance, as shown in FIGS. 3 and 4 of the drawings, so that a balanced treatment for meridians is possible with an equal distribution of magnetic flux for each and every side of the trunk, and this practice should be applied to all magnet sizes used under this trunk method of magnetic application.

Any magnet, permanent or electromagnet, or solid or flexible, may be utilized.

Typically, a flat magnet is employed, thus to provide well contact and substantially equal magnetic flux over the area of the trunk.

In applying magnets to the trunk of a patient, it is desirable that magnets of equal size and total flux are applied evenly to whole area of the trunk and, in addition, for treatment partially by regions of the trunk together, equal time of treatment should be practiced for a balanced treatment. The magnet may have any configuration appropriate to the area to which it is to be applied, such as square, rectangular, circular, oval, disc, bar or flexible. The size of the magnet should be such as to cover the entire regions of the trunk or only the subregions of the trunk or only a part of the subregions, at least more than ⅛" inch diameter.

Practically, any size appropiiate for the trunk is usable, however, the range of the magnet size preferred for this trunk method is from ⅛"×⅛" to (13") 28"×43". Any magnet within this range of size can be effectively used.

In applying magnet means to the trunk, magnet or magnets are attached to the trunk skin in the designated area of the trunk by using elastic band, trunk-shaped wrapper or cover with Velcro fasteners for well conet, as shown in FIGS. 3, 4, 5, 6 and 12 of the drawings.

Elastic band may include wraparound belts to securely hold the magnets sewn-in or encased in fabric lining, or adjustable Velcro type fasteners.

The magnet is positioned so that it is not readily removable or separable from the skin of the trunk of the patient in order to be properly effective.

Magnets should be contacted well to the skin of the trunk at 90 degree angle so that no gab between magnet and skin is allowed. As disclosed in the prior art of the head, neck and two-hand method, the closer contact to the skin for magnet the better for effectiveness and, on the contrary, the farther from the skin the lesser effective.

The method is applicable for all afflictions, ailments and diseases associated with trunk and its meridians. As stated, the method is extremely effective according to the invention, and serves to treat concurrently various or all afflictions and ailments of the entire body of a person. The method also serves to energize the person and relieve tiredness.

Effectiveness and applicability of the method are all observable at treatment site and easily verifiable instantly by patient during treatment in same way as prior art of head, neck and two-hand magnetic method.

Treatment may begin with a relatively low power magnet, with successive application of magnets of increasing strength in accordance with the progress, response and feeling of the patient relative to relief. Typically, response is felt after 15 minutes, and within 30 minutes the patient can sense a cure in progress and a good feeling. Fifteen to ninety minutes of application is the optimum period for most effective treatment of most ailments or diseases.

The treatment time is typically 15 to 180 minutes, typically once or twice daily at interval of about 2–10 hours depending on total flux used and condition of the ailments or as often as needed whenever pain occurs.

The north side of the magnet is applied directly to the area of the trunk and is left in place for 15 to 180 minutes. Pain is typically then gone.

Treatment commences upon application of the magnet and typically extends from 15 to 180 minutes, one or two times per day, at intervals of about 2–10 hours, or as often as needed whenever pain occurs.

At the end of each treatment, the magnet or magnets are removed. Most ailments or diseases are cured or greatly alleviated with one or two treatments.

Treatment may be repeated until complete cure is effected. The treatment may be repeated at intervals in accordance with need and progress. For relatively serious or long-term ailments, treatment may extend for many days, and even for a few months or more. The effectiveness of treatment extends for about four to ten hours after removal of the magnet or magnets. Relatively simple or minor ailments or complaint is cured with one or two treatment.

The criterion used in this invention for therapeutic effectiveness and operativeness was "Did all pains of patient relieved concurrently from whole body within 15 minutes to two hour of each treatment session and did any side effect occurred or accompanied and did patient detect ailment and progress of cure and did patient feel energized".

Applying north pole of the magnet to the designated area of the trunk of the patients, in accordance with the invention, relieves all pains related with the trunk meridians of the body concurrently, regardless of cause and location, showing holistic total effectiveness for whole body of the patient. Of various medical treatments, utilizing magnet means to the trunk in accordance with the invention is found to be very effective to cope with pains and affliction.

In practice of this holistic treatment, cause, location and names of ailments involved are not considered as important factors for treatment because all pains and afflictions associated with various ailments of whole body including chronic diseases are treated holistically and concurrently with excellent result of pain relief and cure, which are all observable and verifiable at site while treated within 15 minutes to three hours with no waiting time period for the treatment result, unlike conventional method. And in addition, patients can detect own ailments and cure in progress and final result as well by symptoms occurred in response to the magnetic application to the trunk, and patients treated become energized and feel a power or strength in arms and wrists, especially when awaked in the morning.

Introduced below shows a typical example of the holistic total treatment for afflictions of all ailments of entire body for which the magnet device and the method were utilized—male patient, 68 years old, suffering from constant pain symptoms of chest-heartburn, stomachache, backache, lumbago, bladder-cystitis, hemorrhoid and neuralgia for many years, was treated with this trunk method by utilizing 13 magnets of 1"D×0,875T" with about 5,000φ total flux for one or two times every day. The pain symptoms were relieved holistically every time treated and the overall pain symptoms were substantially relieved with about two month treatment which is a remarkable result. The patient was able to live normal life in free of pain.

Normally, it is impossible to cure or manage such symptoms in two month with the conventional method.

In proceeding according to the invention, the person or patient is preferably in a prone position or seated or any position comfortable for the application of magnetism. Magnet means may be applied to the trunk while the person is in a standing, sitting, or recline position.

During the treatment, afflictions, ailments and diseases of a person are detected and sensed by the responses and symptoms of the person in response to the application of the magnetism in same way as prior art of two-hand or head or neck magnetic method. The patient may sense responses involving complex symptoms, such as pain, strain, tightness, itch, warmth, coldness, etc. Such symptoms may be mixed and continue until the spot is cured or relieved. The cure in progress is sensed by the person during the application of magnetism in accordance with the invention.

The response or reaction of the patient to the trunk treatment may involve the entire body. Symptoms occur from all diseased or afflicted areas of the body of the patient, and symptoms are usually continued until all ailments and diseases are greatly alleviated or cured. When all ailments are cured, all symptoms and responses are completely gone and this happens only when there is no ailment in the body. Thus there is no symptom or response occurring from healthy body even under magnetic application to the trunk or neck or head or hands. Such phenomenon is all observable and verifiable instantly by patient at treatment site while in treatment. As stated earlier, after application of the magnet for an appropriate time, the patient senses a response and therapeutical effect of cure in progress.

For internal illnesses or ailments or chronic diseases, after 15 minutes of application of the magnets to the trunk, a response or reaction occurs in the patient, and the patient can sense a good response and active curing in 15 to 60 minutes of treatment. After approximately 90 minutes of application of the magnet, the response or reaction of the person's body gradually diminishes, the patient's body becomes relaxed, and a feeling of well-being permeates the patient's body.

This point in time of a treatment may be called as a balanced treatment point.

When balanced point is reached through the course of a treatment whole body becomes relaxed and then all pains and afflictions are gone with a feeling of well being.

At this very moment treatment should be stopped immediately—magnets should be removed from the trunk skin, otherwise, the balance point may be reversed by over-treatment with a result of less effectiveness and a possible side effect.

Therefore, in accordance with the balance concept of Oriental medical theory, the point of being relaxed, easy state of human body occurring during a treatment is believed to be the exact point of a well balanced state of harmony in body systems in treatment. The magnet may typically be applied for 15 to 180 minutes and for not more than 180 minutes of a maximum balanced point, in order to prevent over-balanced treatment. Such balanced point in treatment is also dependent upon and is affected by factors including total flux, distance between magnet and skin, and condition of ailment and thereby each person might have a different balanced point.

However, in most cases, the balance points of treatment are within a range of 15 to 180 minutes. Therefore, the magnets may be applied within the specified time period needed to produce therapeutic effect and the following schedule may preferably be observed in the trunk treatment:

Treatment: 15–180 minutes
Resting time: 2–10 hours
Frequency: 1–2 times daily/whenever pain occurs In application of magnetism to the trunk of body of person, virtually all magnet, permanent and electromagnet, including weak magnets may be used and are all effective, whereas only relatively strong magnets with a total flux of more than 5,000φ are utilized in the referenced prior art of two-hand method. Permanent magnets are preferred for economic reasons, but electromagnets can be utilized to advantage because their power can be varied or desired, within design limitations.

The range of total flux for magnets used is about 30φ–250,000φ and such total flux is measured at 0.001" from the north pole susrface of the magnet means.

The size of the magnet may typically be any size of healing power appropriate for weight and effectiveness for the regions of the trunk of 28"×43".

The effectiveness and curative results increase with increase of flux density(gauss) and total flux of the magnet applied to the person.

Thereby, using "total flux" provides a flexibility of options to select and control healing power, weight, pulling/repelling distance and treatment time period based on type of ailment, size of treatment area or region to apply and treatment progress thereof, etc., whereas other means of magnetic strength measured by gauss, flux density and magnet size alone do not provide such options of healing power control and adjustment to meet a real challenge of treating various levels of sickness from a mild to a severe condition. Therefore, using total flux in present invention is unique and consistent throughout the entire period of 25 years research since 1980 for handling all levels of severity of the afflictions, ailments and diseases producing a desirable effectiveness under all situations of imbalance and disorder of the meridians.

Therefore, the total flux applied to the patient is considered to be of key importance in selection of desired healing power, treatment time period and its weight appropriate for trunk regions.

The following formula sets forth the relationship between total flux, flux density and magnet pole area:

$$\phi = BA$$

Where
φ=total flux
B=flux density in gauss
A=area

Magnetic application to the trunk has been found to be very safe, however, only for precaution, magnets should not be utilized in treating infants, pregnant women and person with heart pacemaker or metal implanted.

Thus there has been shown and described a novel treatment of afflictions and ailments with magnetism which fulfills all the objects and advantages sought therefore.

Many changes, modifications, variations and other uses and applications of the subject invention will, however, become apparent to those skilled in the art after considering this specification together with the accompanying drawings and claims.

All such changes, modifications, variations and other uses and applications which do not depart from the spirit and scope of the invention are deemed to be covered by the invention which is limited only by the claims which follow.

The invention claimed is:

1. A method of treating and alleviating human afflictions, ailments and diseases holistically by application of magnetism to a plurality of treating regions of the trunk of a person being treated in such way to bring the body meridian systems into a balance and harmony, the method comprises the steps of:

providing magnet means having at least one north pole surface adapted for application to said plurality of treating regions of the trunk, said north pole surface being in direct contact with the surface of said trunk;

designating a total treating region to the trunk having a total size of about 1204 square inches, covering about 28"×43" of the total trunk region all the way around said trunk, said total treating region being divided into at least first, second and third treating regions, according to shape of the trunk and meridian balance structure;

applying the north pole surface of said magnet means to at least one of said treating regions of the trunk, said magnet means having a size and shape appropriate to cover at least part of one of said treating regions of the trunk; and maintaining said magnet means in contact with the at least one of said treating regions of the trunk for a period of 15 to 180 minutes to heal and relieve afflictions, wherein the total flux of said magnetic means applied to the at least one of said treating regions of the trunk being in the range from about 1000φ–250,000φ.

2. The method of claim 1, further including the step of repeating the application of the magnet means for at least one additional period of time.

3. The method of claim 1, further comprising repeating the time period for treatment at least once in a 24 hour period in an interval of about 2–10 hours in accordance with treatment progress.

4. The method of claim 1, further including: applying the magnet means to said first, second and third treating regions, said first treating region representing the chest and upper back part, said second treating region representing the upper abdominal and middle back part and said third treating region representing the lower abdominal and lower back part of the trunk.

5. The method of claim 1, further including applying the magnet means to said treating regions in order, or in reverse order.

6. The method of claim 1, further including first applying the magnet means to said first treating region of the trunk of the person and then applying the magnet means to said second treating region of the trunk of the person.

7. The method of claim 1, further including applying said magnet means to said first and second treating regions of the trunk of a person concurrently.

8. The method of claim 1, further including applying the magnet means to all said first, second and third treating regions of the trunk of a person concurrently.

9. The method of claim 1, wherein the total flux of the magnet applied to said first, second and third treating regions of the trunk of the person is substantially equal.

10. The method of claim 1, further comprising applying said magnet means to said first, second and third treating regions concurrently by disposing the magnet in horizontal order all the way around the trunk in parallel to a horizontal waist line of the trunk so that all the meridians disposed in the trunk of the body are treated simultaneously and equally in balance for a balanced treatment.

11. The method of claim 1, further comprising applying said magnet means to said first, second and third treating regions concurrently by disposing said magnet means in horizontal order all the way around the trunk in parallel to a horizontal waistline of the trunk so that all the meridians disposed in the trunk of the body are treated simultaneously and equally in balance for a balanced treatment.

12. The method of claim 1, further comprising applying multiple magnet means to said first, second and third treating regions concurrently by disposing said magnet means evenly, spaced apart, at an equal distance, throughout said treating regions so that all parts of the treating regions of the trunk of a person are treated equally with total magnetic flux for a balanced treatment.

13. The method of claim 1, further comprising applying additional magnet means of substantially equal total flux to said first, second and third treating regions of the trunk of the person for a balanced treatment.

14. The method of claim 1, further comprising applying said magnet means consecutively or at intervals to said first, second or third treating regions of the trunk of the person for equal time periods for a balanced treatment.

15. The method of claim 1, further comprising substantially covering the entire surface of said first, second and third treating regions of the trunk with the north pole surface of said magnet means.

16. The method of claim 1, further comprising partially covering the surface of said first, second and third treating regions of the trunk with the north pole surface of said magnet means.

17. The method of claim 1, further including maintaining contact of the magnet means for a time period sufficient for the person to produce a pain mitigation and relief from ailing part of the body.

18. The method of claim 1, further providing retaining means for holding said magnet means to the trunk to provide effective contact of the north pole surface of said magnet means with the trunk.

* * * * *